(12) United States Patent
Demers et al.

(10) Patent No.: US 10,478,261 B2
(45) Date of Patent: Nov. 19, 2019

(54) SYSTEM, METHOD, AND APPARATUS FOR REMOTE PATIENT CARE

(71) Applicant: DEKA Products Limited Partnership, Manchester, NH (US)

(72) Inventors: Jason A. Demers, Manchester, NH (US); Frederick Morgan, Canton, MA (US); George W. Marchant, Jr., Goffstown, NH (US); David E. Collins, Merrimac, MA (US); Katie A. DeLaurentis, Manchester, NH (US); Dean Kamen, Bedford, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 15/163,906

(22) Filed: May 25, 2016

(65) Prior Publication Data
US 2016/0346056 A1 Dec. 1, 2016

Related U.S. Application Data

(60) Provisional application No. 62/168,343, filed on May 29, 2015.

(51) Int. Cl.
*A61B 50/31* (2016.01)
*A61B 5/022* (2006.01)
(Continued)

(52) U.S. Cl.
CPC ........ *A61B 50/31* (2016.02); *A61B 5/150022* (2013.01); *A61B 5/150305* (2013.01);
(Continued)

(58) Field of Classification Search
None
See application file for complete search history.

(56) References Cited

U.S. PATENT DOCUMENTS 5,801,755 A * 9/1998 Echerer ............... A61B 5/0002
348/14.01
8,016,089 B1 * 9/2011 McNichols ............ A45C 5/14
190/1
(Continued)

FOREIGN PATENT DOCUMENTS

WO WO2013095459 A9 6/2013
WO WO2013096713 A2 6/2013
(Continued)

OTHER PUBLICATIONS

Adler, Ari T., "A Cost-Effective Portable Telemedicine Kit for Use in Developing Countries"; Thesis; Brandeis University, 1996; May 19, 2000; © 2000 Massachusetts Institute of Technology; pp. 1-96.
(Continued)

*Primary Examiner* — Idriss N Alrobaye
*Assistant Examiner* — Dayton Lewis-Taylor
(74) *Attorney, Agent, or Firm* — James D. Wyninegar, Jr.

(57) ABSTRACT

A portable patient-care kit is disclosed. The kit includes two-housing portions, a plurality of compartments, a touch-screen user interface device, and a light bar. The two-housing portions pivotally coupled together to form a container space. The plurality of compartments is disposed within at least one of the housing portions such that each compartment is configured to retain at least one medical apparatus. The touch-screen user interface device has a transceiver that can communicate via a mobile data network. The light bar is disposed along an exterior of one of the two-housing portions configured provide light.

49 Claims, 8 Drawing Sheets

(51) Int. Cl.

| | |
|---|---|
| *A61B 5/1455* | (2006.01) |
| *A61B 34/00* | (2016.01) |
| *A61B 10/00* | (2006.01) |
| *A61B 90/30* | (2016.01) |
| *A61B 90/98* | (2016.01) |
| *B65D 5/00* | (2006.01) |
| *A61M 16/00* | (2006.01) |
| *A61M 16/10* | (2006.01) |
| *G06F 19/00* | (2018.01) |
| *A61B 5/15* | (2006.01) |
| *A61B 50/30* | (2016.01) |
| *A61B 50/00* | (2016.01) |
| *A61B 17/00* | (2006.01) |
| *A61B 5/157* | (2006.01) |
| *G16H 40/60* | (2018.01) |
| *G16H 40/63* | (2018.01) |
| *G16H 10/65* | (2018.01) |

(52) U.S. Cl.
CPC ............ *A61B 10/007* (2013.01); *A61B 34/25* (2016.02); *A61B 90/30* (2016.02); *A61B 90/98* (2016.02); *A61M 16/0051* (2013.01); *A61M 16/021* (2017.08); *A61M 16/10* (2013.01); *B65D 5/0085* (2013.01); *G06F 19/34* (2013.01); *A61B 5/157* (2013.01); *A61B 5/150343* (2013.01); *A61B 2017/00199* (2013.01); *A61B 2017/00221* (2013.01); *A61B 2017/00734* (2013.01); *A61B 2050/0056* (2016.02); *A61B 2050/3008* (2016.02); *A61B 2050/311* (2016.02); *A61B 2560/0252* (2013.01); *A61B 2560/0257* (2013.01); *A61B 2562/029* (2013.01); *A61B 2562/182* (2013.01); *A61M 2202/0208* (2013.01); *A61M 2205/15* (2013.01); *A61M 2205/18* (2013.01); *A61M 2205/3569* (2013.01); *A61M 2205/3592* (2013.01); *A61M 2205/581* (2013.01); *A61M 2205/583* (2013.01); *A61M 2205/6054* (2013.01); *A61M 2209/06* (2013.01); *A61M 2209/084* (2013.01); *A61M 2230/04* (2013.01); *A61M 2230/205* (2013.01); *A61M 2230/30* (2013.01); *A61M 2230/50* (2013.01); *G16H 10/65* (2018.01); *G16H 40/60* (2018.01); *G16H 40/63* (2018.01)

(56) References Cited

U.S. PATENT DOCUMENTS

| | | | | |
|---|---|---|---|---|
| 8,434,577 | B1* | 5/2013 | Al-Qaffas | A45C 13/24 |
| | | | | 180/65.1 |
| D728,779 | S | 5/2015 | Sabin et al. | |
| D735,319 | S | 7/2015 | Sabin et al. | |
| D736,370 | S | 8/2015 | Sabin et al. | |
| 9,106,421 | B1* | 8/2015 | Singh | H04L 9/0827 |
| 9,151,646 | B2 | 10/2015 | Kamen et al. | |
| D745,661 | S | 12/2015 | Collins et al. | |
| D749,206 | S | 2/2016 | Johnson et al. | |
| D751,689 | S | 3/2016 | Peret et al. | |
| D751,690 | S | 3/2016 | Peret et al. | |
| D752,209 | S | 3/2016 | Peret et al. | |
| 9,295,778 | B2 | 3/2016 | Kamen et al. | |
| D754,065 | S | 4/2016 | Gray et al. | |
| D756,386 | S | 5/2016 | Kendler et al. | |
| D758,399 | S | 6/2016 | Kendler et al. | |
| D760,288 | S | 6/2016 | Kendler et al. | |
| D760,289 | S | 6/2016 | Kendler et al. | |
| 9,364,394 | B2 | 6/2016 | Demers et al. | |
| 9,372,486 | B2 | 6/2016 | Peret et al. | |
| D760,782 | S | 7/2016 | Kendler et al. | |
| D760,888 | S | 7/2016 | Gill et al. | |
| 9,400,873 | B2 | 7/2016 | Kamen et al. | |
| D767,756 | S | 9/2016 | Sabin | |
| 9,435,455 | B2 | 9/2016 | Peret et al. | |
| D768,716 | S | 10/2016 | Kendler et al. | |
| 9,465,919 | B2 | 10/2016 | Kamen et al. | |
| 9,488,200 | B2 | 11/2016 | Kamen et al. | |
| 2002/0001794 | A1* | 1/2002 | Melker | G09B 7/02 |
| | | | | 434/350 |
| 2007/0095914 | A1* | 5/2007 | Noguchi | G06K 7/0004 |
| | | | | 235/451 |
| 2007/0135965 | A1* | 6/2007 | Nguyen | A61G 12/001 |
| | | | | 700/231 |
| 2007/0272746 | A1* | 11/2007 | Ortiz | G06K 17/00 |
| | | | | 235/385 |
| 2009/0108011 | A1 | 4/2009 | Heffron | |
| 2010/0235782 | A1* | 9/2010 | Powell | G06F 19/3418 |
| | | | | 715/809 |
| 2011/0102146 | A1* | 5/2011 | Giron | G01S 13/74 |
| | | | | 340/7.62 |
| 2011/0197887 | A1* | 8/2011 | Truschel | A61M 16/0051 |
| | | | | 128/204.23 |
| 2011/0313789 | A1 | 12/2011 | Kamen et al. | |
| 2012/0095779 | A1* | 4/2012 | Wengrovitz | G06Q 50/24 |
| | | | | 705/3 |
| 2012/0185267 | A1 | 7/2012 | Kamen | |
| 2012/0197090 | A1* | 8/2012 | Chen | A61B 5/14532 |
| | | | | 600/301 |
| 2013/0023741 | A1* | 1/2013 | Ayanruoh | A61B 13/00 |
| | | | | 600/301 |
| 2013/0043826 | A1* | 2/2013 | Workman | H01M 2/0245 |
| | | | | 320/101 |
| 2013/0152175 | A1* | 6/2013 | Hromoko | H04W 36/0011 |
| | | | | 726/5 |
| 2013/0176115 | A1* | 7/2013 | Puleston | H04L 67/04 |
| | | | | 340/10.51 |
| 2013/0177455 | A1 | 7/2013 | Kamen | |
| 2013/0182381 | A1 | 7/2013 | Gray | |
| 2013/0184676 | A1 | 7/2013 | Kamen | |
| 2013/0188040 | A1 | 7/2013 | Kamen | |
| 2013/0191513 | A1 | 7/2013 | Kamen | |
| 2013/0197693 | A1 | 8/2013 | Kamen | |
| 2013/0204188 | A1 | 8/2013 | Kamen | |
| 2013/0272773 | A1 | 10/2013 | Kamen | |
| 2013/0281965 | A1 | 10/2013 | Kamen | |
| 2013/0297330 | A1 | 11/2013 | Kamen | |
| 2013/0310990 | A1 | 11/2013 | Peret et al. | |
| 2013/0317753 | A1 | 11/2013 | Kamen | |
| 2013/0317837 | A1 | 11/2013 | Ballantyne | |
| 2013/0336814 | A1 | 12/2013 | Kamen | |
| 2013/0339049 | A1 | 12/2013 | Blumberg, Jr. | |
| 2013/0346108 | A1 | 12/2013 | Kamen | |
| 2014/0064164 | A1* | 3/2014 | Nagaraj | H04W 52/0206 |
| | | | | 370/311 |
| 2014/0128757 | A1* | 5/2014 | Banet | A61B 5/053 |
| | | | | 600/513 |
| 2014/0165703 | A1 | 6/2014 | Wilt | |
| 2014/0180711 | A1 | 6/2014 | Kamen | |
| 2014/0188076 | A1 | 7/2014 | Kamen | |
| 2014/0188516 | A1 | 7/2014 | Kamen | |
| 2014/0195639 | A1 | 7/2014 | Kamen | |
| 2014/0227021 | A1 | 8/2014 | Kamen | |
| 2014/0246991 | A1* | 9/2014 | Kim | H05B 37/0227 |
| | | | | 315/292 |
| 2014/0318639 | A1 | 10/2014 | Peret | |
| 2014/0330428 | A1* | 11/2014 | Wolfe | B65G 51/44 |
| | | | | 700/226 |
| 2014/0343492 | A1 | 11/2014 | Kamen | |
| 2014/0379848 | A1* | 12/2014 | Sabbouh | H04L 67/10 |
| | | | | 709/217 |
| 2015/0002667 | A1 | 1/2015 | Peret et al. | |
| 2015/0002668 | A1 | 1/2015 | Peret et al. | |
| 2015/0002677 | A1 | 1/2015 | Peret et al. | |
| 2015/0033823 | A1 | 2/2015 | Blumberg, Jr. | |
| 2015/0314083 | A1 | 4/2015 | Blumberg, Jr. et al. | |
| 2015/0137997 | A1* | 5/2015 | Huang | A61B 5/1112 |
| | | | | 340/870.09 |

(56) References Cited

U.S. PATENT DOCUMENTS

| | | | |
|---|---|---|---|
| 2015/0151051 A1* | 6/2015 | Tsoukalis | A61M 5/1723 604/67 |
| 2015/0154364 A1 | 6/2015 | Biasi et al. | |
| 2015/0157791 A1 | 6/2015 | Desch et al. | |
| 2015/0192993 A1* | 7/2015 | Pellaton | G06F 3/014 340/10.5 |
| 2015/0237217 A1* | 8/2015 | Roark | H04M 19/001 455/556.1 |
| 2015/0238228 A1 | 8/2015 | Langenfeld et al. | |
| 2015/0257974 A1 | 9/2015 | Demers et al. | |
| 2015/0332009 A1 | 11/2015 | Kane et al. | |
| 2016/0055397 A1 | 2/2016 | Peret et al. | |
| 2016/0055649 A1 | 2/2016 | Peret et al. | |
| 2016/0061641 A1 | 3/2016 | Peret et al. | |
| 2016/0063353 A1 | 3/2016 | Peret et al. | |
| 2016/0073063 A1 | 3/2016 | Peret et al. | |
| 2016/0084434 A1 | 3/2016 | Janway et al. | |
| 2016/0097382 A1 | 4/2016 | Kamen et al. | |
| 2016/0131272 A1 | 5/2016 | Yoo et al. | |
| 2016/0158437 A1 | 6/2016 | Biasi et al. | |
| 2016/0179086 A1 | 6/2016 | Peret et al. | |
| 2016/0184510 A1 | 6/2016 | Kamen et al. | |
| 2016/0203292 A1 | 7/2016 | Kamen et al. | |
| 2016/0262977 A1 | 9/2016 | Demers et al. | |
| 2016/0319850 A1 | 11/2016 | Kamen et al. | |
| 2016/0328900 A1* | 11/2016 | Yong | G07C 9/00309 |

FOREIGN PATENT DOCUMENTS

| | | | |
|---|---|---|---|
| WO | WO2013096718 | A2 | 6/2013 |
| WO | WO2013096722 | A2 | 6/2013 |
| WO | WO2013096909 | A2 | 6/2013 |
| WO | WO2013176770 | A2 | 11/2013 |
| WO | WO2013177357 | A1 | 11/2013 |
| WO | WO2014100557 | A2 | 6/2014 |
| WO | WO2014100571 | A2 | 6/2014 |
| WO | WO2014100658 | A1 | 6/2014 |
| WO | WO2014100687 | A2 | 6/2014 |
| WO | WO2014100736 | A2 | 6/2014 |
| WO | WO2014100744 | A2 | 6/2014 |
| WO | WO2014144557 | A2 | 9/2014 |
| WO | WO2015017275 | A1 | 2/2015 |
| WO | WO2016/090315 | A1 | 6/2016 |

OTHER PUBLICATIONS

AMD Global Telemedicine; "A Collaborative Patient Assessment Tool for Telemedicine Clinical Exams"; AGNES Interactive®; www.amdtelemedicine.com; info@amdtelemedicine.com; 321 Billerica Road, Chelmsford, MA 01824; Rev. Jan. 28, 2016; pp. 1-2.

AMD Global Telemedicine; Portable TeleClinic™ "Clinical Telemedicine in a Mobile Case"; http://www.amdtelemedicine.com/telemedicine-equipment/portable-teleclinic.html; May 26, 2016; pp. 1-2.

Becky; Albert Schweitzer Hospital; "VSee Telemedicine Kit Brings Harvard Doctors to Gabon Villagers"; Posted Jul. 18/ By becky (https://vsee.com/blog/author/becky/) / In Telemedicine News (https://vsee.com/blog/category/telemedicine-news/), VSee (https://vsee.co/blog/category/vsee/); https://vsee.com/blog/vsee-telemedicine-kit-in-africa/; May 26, 2016; pp. 1-14.

DIGIGONE Remote Communication Solutions; "Knock Big Data down to size" "Remote Camera Kit"; sales@digigone.com; http://www.digigone.com/remote_cam_kit.php; May 26, 2016; p. 1.

VSee Telemedicine; "Simple, Secure Telemedicine Solutions"; VSee Telemedicine Kit—In Gabon and Beyond; https://vsee.com/telemedicine; May 26, 2016; ©2016 VSee; pp. 1-11.

United States Patent and Trademark Office (USPTO); William R. Wright (For Patent Owner) David L. Stewart (For Requestor); In re Campana, Jr. et al., inter partes Reexamination Proceeding, Control No. 95/000,020, Filed May 29, 2003, for U.S. Pat. No. 6,317,592, Paper No. 15; Mailed Jun. 2, 2004, Reexam Unit; Decision Dismissing Petition; pp. 1-969.

VSee Video Telemedicine; VSee Product Catalog Web; ©2015VSee p. 1.
U.S. Appl. No. 61/297,544, filed Jan. 22, 2010.
U.S. Appl. No. 13/011,543, filed Jan. 21, 2011, US20110313789A1.
U.S. Appl. No. 61/578,674, filed Dec. 21, 2011.
U.S. Appl. No. 13/333,574, filed Dec. 21, 2011, US20120185267A1.
PCT/US11/66588, Dec. 21, 2011, WO2013095459A1.
U.S. Appl. No. 61/578,649, filed Dec. 21, 2011.
U.S. Appl. No. 61/578,658, filed Dec. 21, 2011.
U.S. Appl. No. 61/651,322, filed May 24, 2012.
U.S. Appl. No. 61/679,117, filed Aug. 3, 2012.
U.S. Appl. No. 61/738,447, filed Dec. 18, 2012.
U.S. Appl. No. 13/723,238, filed Dec. 21, 2012, US20130182381A1.
U.S. Appl. No. 13/723,242, filed Dec. 21, 2012, US20130317753A1.
PCT/US12/71112, Dec. 21, 2012, WO2013096713A1.
U.S. Appl. No. 13/723,251, filed Dec. 21, 2012, US20130204188A1.
U.S. Appl. No. 61/740,474, filed Dec. 21, 2012.
PCT/US12/71142, Dec. 21, 2012, WO2013096722A1.
U.S. Appl. No. 13/723,244, filed Dec. 21, 2012, US20130188040A1.
U.S. Appl. No. 13/723,239, filed Dec. 21, 2012, US20130297330A1.
PCT/US12/71490, Dec. 21, 2012, WO2013096909A1.
U.S. Appl. No. 13/725,790, filed Dec. 21, 2012, US20130177455A1.
U.S. Appl. No. 13/723,253, filed Dec. 21, 2012, US20130191513A1.
PCT/US12/71131, Dec. 21, 2012, WO2013096718A1.
U.S. Appl. No. 13/723,235, filed Dec. 21, 2012, US20130197693A1.
U.S. Appl. No. 13/724,568, filed Dec. 21, 2012, US20130184676A1.
U.S. Appl. No. 13/833,432, filed Mar. 15, 2013, US20130281965A1.
U.S. Appl. No. 13/833,712, filed Mar. 15, 2013, US20130272773A1.
PCT/US13/32445, Mar. 15, 2013, WO2013176770A1.
U.S. Appl. No. 13/836,497, filed Mar. 15, 2013, US20130346108A1.
U.S. Appl. No. 13/834,030, filed Mar. 15, 2013, US20130310990A1.
U.S. Appl. No. 13/840,339, filed Mar. 15, 2013, US20130336814A1.
PCT/US13/42350, May 23, 2013, WO/2013/177357A1.
U.S. Appl. No. 13/900,655, filed May 23, 2013, US20130317837A1.
U.S. Appl. No. 29/457,516, filed Jun. 11, 2013, USD0728779S.
U.S. Appl. No. 29/457,520, filed Jun. 11, 2013, USD0735319S.
U.S. Appl. No. 29/457,522, filed Jun. 11, 2013, USD0736370S.
U.S. Appl. No. 29/457,521, filed Jun. 11, 2013.
U.S. Appl. No. 61/843,574, filed Jul. 8, 2013.
U.S. Appl. No. 61/860,398, filed Jul. 31, 2013.
U.S. Appl. No. 13/971,258, filed Aug. 20, 2013, US20130339049A1.
U.S. Appl. No. 61/894,801, filed Oct. 23, 2013.
U.S. Appl. No. 29/471,864, filed Nov. 6, 2013, USD0752209S.
U.S. Appl. No. 61/900,431, filed Nov. 6, 2013.
U.S. Appl. No. 29/471,856, filed Nov. 6, 2013, USD0751689S.
U.S. Appl. No. 29/471,858, filed Nov. 6, 2013, USD0751690S.
U.S. Appl. No. 29/471,859, filed Nov. 6, 2013, USD0745661S.
U.S. Appl. No. 29/471,861, filed Nov. 6, 2013, USD0749206S.
U.S. Appl. No. 61/904,123, filed Nov. 14, 2013.
U.S. Appl. No. 14/101,848, filed Dec. 10, 2013, US20140165703A1.
U.S. Appl. No. 29/477,231, filed Dec. 20, 2013.
U.S. Appl. No. 29/477,242, filed Dec. 20, 2013, USD0756386S.
U.S. Appl. No. 29/477,237, filed Dec. 20, 2013.
U.S. Appl. No. 29/477,236, filed Dec. 20, 2013.
U.S. Appl. No. 29/477,233, filed Dec. 20, 2013.
U.S. Appl. No. 29/477,249, filed Dec. 20, 2013.
U.S. Appl. No. 29/477,232, filed Dec. 20, 2013.
PCT/US13/76851, Dec. 20, 2013, WO2014100557A1.
PCT/US13/77135, Dec. 20, 2013, WO/2014/100687A1.
U.S. Appl. No. 14/136,243, filed Dec. 20, 2013, US20140188516A1.
PCT/US13/77258, Dec. 20, 2013, WO2014100736A1.
U.S. Appl. No. 14/137,421, filed Dec. 20, 2013, US20140180711A1.
PCT/US13/77270, Dec. 20, 2013, WO/2014/100744A1.
U.S. Appl. No. 14/135,809, filed Dec. 20, 2013, US20140195639A1.
PCT/US13/76886, Dec. 20, 2013, WO/2014/100571A1.
U.S. Appl. No. 14/135,784, filed Dec. 20, 2013, US20140188076A1.
PCT/US13/77077, Dec. 20, 2013, WO/2014/100658A1.
U.S. Appl. No. 14/137,562, filed Dec. 20, 2013, US20140227021A1.
U.S. Appl. No. 61/942,986, filed Feb. 21, 2014.
U.S. Appl. No. 61/953,036, filed Mar. 14, 2014.
U.S. Appl. No. 14/213,373, filed Mar. 14, 2014, US20140318639A1.
PCT/US14/29020, Mar. 14, 2014, WO/2014/144557A1.
U.S. Appl. No. 61/987,742, filed May 2, 2014.

(56) References Cited

OTHER PUBLICATIONS

U.S. Appl. No. 61/990,330, filed May 8, 2014.
U.S. Appl. No. 14/341,207, filed Jul. 25, 2014, US20150033823A1.
PCT/US2014/48227, Jul. 25, 2014, WO2015017275A1.
U.S. Appl. No. 14/451,904, filed Aug. 5, 2014, US20140343492A1.
U.S. Appl. No. 62/052,008, filed Sep. 18, 2014.
U.S. Appl. No. 14/491,161, filed Sep. 19, 2014, US20150002677A1.
U.S. Appl. No. 14/491,143, filed Sep. 19, 2014, US20150002668A1.
U.S. Appl. No. 14/491,128, filed Sep. 19, 2014, US20150002667A1.
U.S. Appl. No. 62/086,356, filed Dec. 2, 2014.
U.S. Appl. No. 14/616,079, filed Feb. 6, 2015, US20150154364A1.
U.S. Appl. No. 29/517,100, filed Feb. 10, 2015.
U.S. Appl. No. 29/517,095, filed Feb. 10, 2015.
U.S. Appl. No. 29/517,096, filed Feb. 10, 2015.
U.S. Appl. No. 29/517,097, filed Feb. 10, 2015.
U.S. Appl. No. 29/517,098, filed Feb. 10, 2015, USD0754065S.
U.S. Appl. No. 29/517,099, filed Feb. 10, 2015.
U.S. Appl. No. 29/517,101, filed Feb. 10, 2015.
U.S. Appl. No. 14/627,287, filed Feb. 20, 2015, US20150157791A1.
PCT/US15/16796, Feb. 27, 2015.
U.S. Appl. No. 14/656,945, filed Mar. 13, 2015, US20150257974A1.
U.S. Appl. No. 14/679,364, filed Apr. 6, 2015, US20150314083A1.
U.S. Appl. No. 62/168,343, filed May 29, 2015.
U.S. Appl. No. 29/531,366, filed Jun. 25, 2015.
U.S. Appl. No. 29/532,660, filed Jul. 9, 2015.
U.S. Appl. No. 14/812,149, filed Jul. 29, 2015, US20150332009A1.
U.S. Appl. No. 62/212,871, filed Sep. 1, 2015.
U.S. Appl. No. 29/538,153, filed Sep. 1, 2015.
PCT/US15/49952, Sep. 14, 2015.
U.S. Appl. No. 14/853,300, filed Sep. 14, 2015.
U.S. Appl. No. 14/873,515, filed Oct. 2, 2015, US20160097382A1.
U.S. Appl. No. 14/932,291, filed Nov. 4, 2015, US20160055649A1.
U.S. Appl. No. 14/931,928, filed Nov. 4, 2015, US20160055397A1.
U.S. Appl. No. 14/938,368, filed Nov. 11, 2015, US20160061641A1.
U.S. Appl. No. 14/938,083, filed Nov. 11, 2015, US20160073063A1.
U.S. Appl. No. 14/939,586, filed Nov. 12, 2015.
U.S. Appl. No. 14/939,015, filed Nov. 12, 2015, US20160063353A1.
PCT/US2015/63359, Dec. 2, 2015.
U.S. Appl. No. 14/956,648, filed Dec. 2, 2015, US20160084434A1.
U.S. Appl. No. 29/547,402, filed Dec. 3, 2015.
U.S. Appl. No. 29/547,405, filed Dec. 3, 2015.
U.S. Appl. No. 29/548,225, filed Dec. 11, 2015.
U.S. Appl. No. 29/552,303, filed Jan. 21, 2016.
U.S. Appl. No. 29/552,942, filed Jan. 27, 2016.
U.S. Appl. No. 29/553,943, filed Jan. 27, 2016.
U.S. Appl. No. 29/553,094, filed Jan. 28, 2016.
U.S. Appl. No. 62/288,132, filed Jan. 28, 2016.
U.S. Appl. No. 29/556,048, filed Feb. 26, 2016.
U.S. Appl. No. 15/055,941, filed Feb. 29, 2016.
U.S. Appl. No. 15/059,394, filed Mar. 3, 2016.
U.S. Appl. No. 15/077,389, filed Mar. 22, 2016.
U.S. Appl. No. 29/561,572, filed Apr. 18, 2016.
U.S. Appl. No. 29/564,750, filed May 16, 2016.
U.S. Appl. No. 15/161,876, filed May 23, 2016.
U.S. Appl. No. 29/565,908, filed May 25, 2016.
U.S. Appl. No. 14/191,827, filed Feb. 27, 2014, US20150238228A1.
U.S. Appl. No. 62/341,396, filed May 25, 2016.
U.S. Appl. No. 29/569,450, filed Jun. 28, 2016.
U.S. Appl. No. 29/569,460, filed Jun. 28, 2016.
U.S. Appl. No. 15/205,538, filed Jul. 8, 2016, US20160319850A1.
U.S. Appl. No. 29/570,648, filed Jul. 11, 2016.
U.S. Appl. No. 29/575,387, filed Jul. 18, 2016.
U.S. Appl. No. 29/575,331, filed Aug. 24, 2016.
U.S. Appl. No. 29/575,316, filed Aug. 24, 2016.
U.S. Appl. No. 15/248,200, filed Aug. 26, 2016, US20160362234A1.
U.S. Appl. No. 15/270,321, filed Sep. 20, 2016, US20170011202A1.
U.S. Appl. No. 15/341,611, filed Nov. 2, 2016, US20170045478A1.
U.S. Appl. No. 15/418,096, filed Jan. 27, 2017.
PCT/US2017/15382, Jan. 27, 2017.
U.S. Appl. No. 15/467,196, filed Mar. 23, 2017.
U.S. Appl. No. 15/584,376, filed May 2, 2017.
U.S. Appl. No. 15/607,776, filed May 30, 2017.

\* cited by examiner

SYSTEM, METHOD, AND APPARATUS FOR REMOTE PATIENT CARE

CROSS REFERENCE TO RELATED APPLICATIONS

The present application is a Non-Provisional Application which claims the benefit of U.S. Provisional Patent Application Ser. No. 62/168,343, filed May 29, 2015 and entitled System, Method, and Apparatus for Remote Patient Care, which is hereby incorporated herein by reference in its entirety.

BACKGROUND

Relevant Field

The present disclosure relates to patient care. More particularly, the present disclosure relates to a system, method and apparatus for using a kit for providing patient care.

Description of Related Art

Healthcare may be delivered in a centralized, decentralized or hybride mode of care. For example, healthcare may be performed by a centralized institution or by smaller, localized care (e.g., in-home care). As care networks look to improve the value of every dollar spent they are learning that alternate care models, and hence environments, have the potential to both decrease expenditures and increase results. One of the key ingredients in this future ecosystem is the interplay between home care and retail medicine.

Some patients may be admitted to a healthcare institution that could potentially receive the same, or better, care at home using a leaner, more agile care model. To facilitate this type of care, patients will need access to the appropriate medical supplies and monitoring the patient would typically receive in a hospital bed with the aid of professional caregivers. Further, the professional caregiver will need an easy and predictable way to transform the patients residence into a recovery area outfitted with the appropriate technology to meet both the patient and the caregiver's needs.

SUMMARY

In accordance with one aspect of the present disclosure, a portable patient-care kit is provided. The kit includes two-housing portions, a plurality of compartments, a touch-screen user interface device, and a light bar. The two-housing portions pivotally coupled together to form a container space. The plurality of compartments is disposed within at least one of the housing portions such that each compartment is configured to retain at least one medical apparatus. The touch-screen user interface device has a transceiver that can communicate via a mobile data network. The light bar is disposed along an exterior of one of the two-housing portions configured provide light. The claims describe exemplary aspects and embodiments.

BRIEF DESCRIPTION OF THE DRAWINGS

These and other aspects will become more apparent from the following detailed description of the various embodiments of the present disclosure with reference to the drawings wherein.

DETAILED DESCRIPTION

Figure 1:
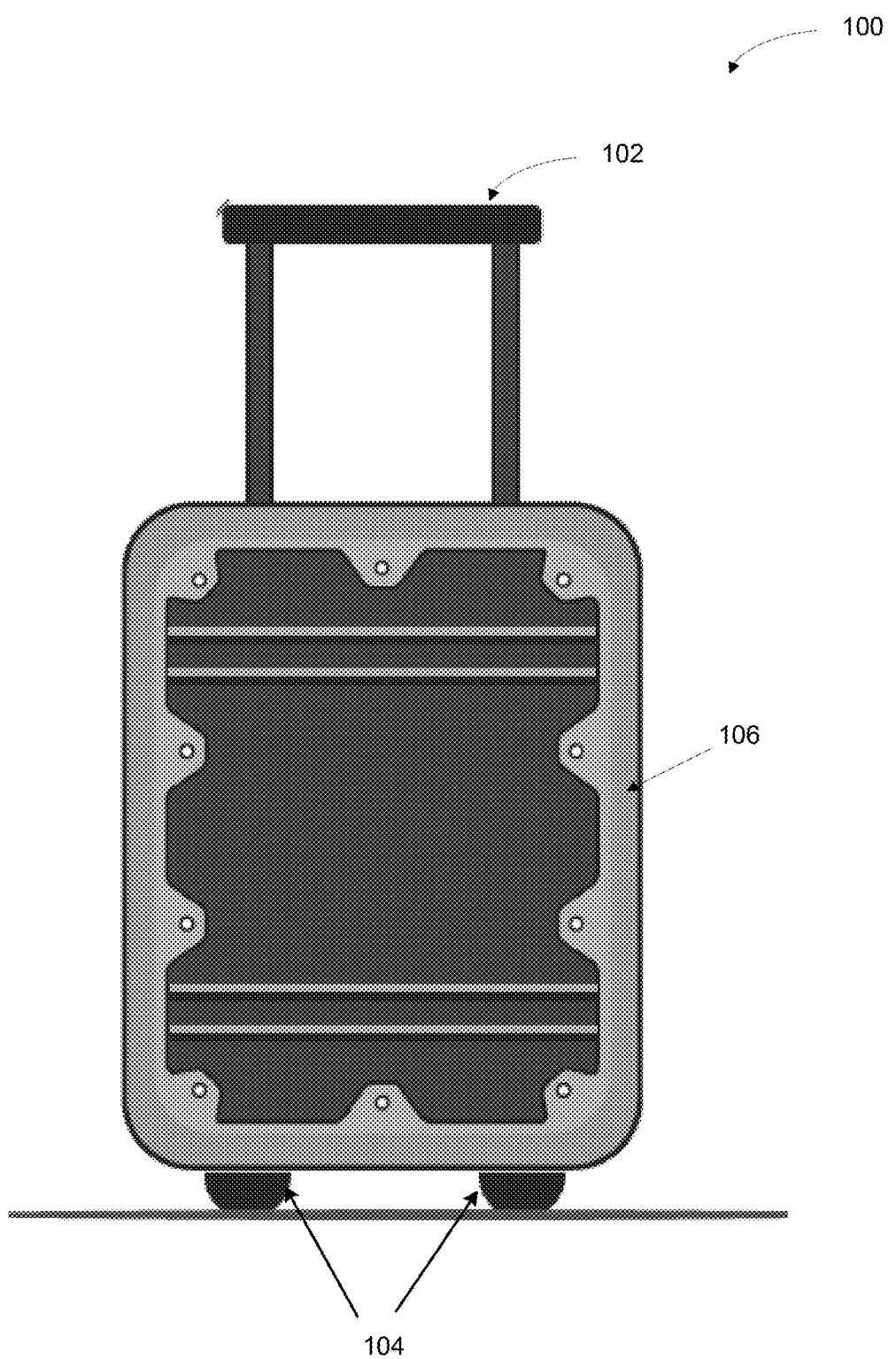
FIG. 1 shows a portable kit for patient care in a transportation configuration in accordance with an embodiment of the present disclosure.

FIG. 1 shows a portable kit 100 for patient care in transportation configuration in accordance with an embodiment of the present disclosure. The kit includes wheels 104 and a handle 102 to facilitate portability.

Figure 2:
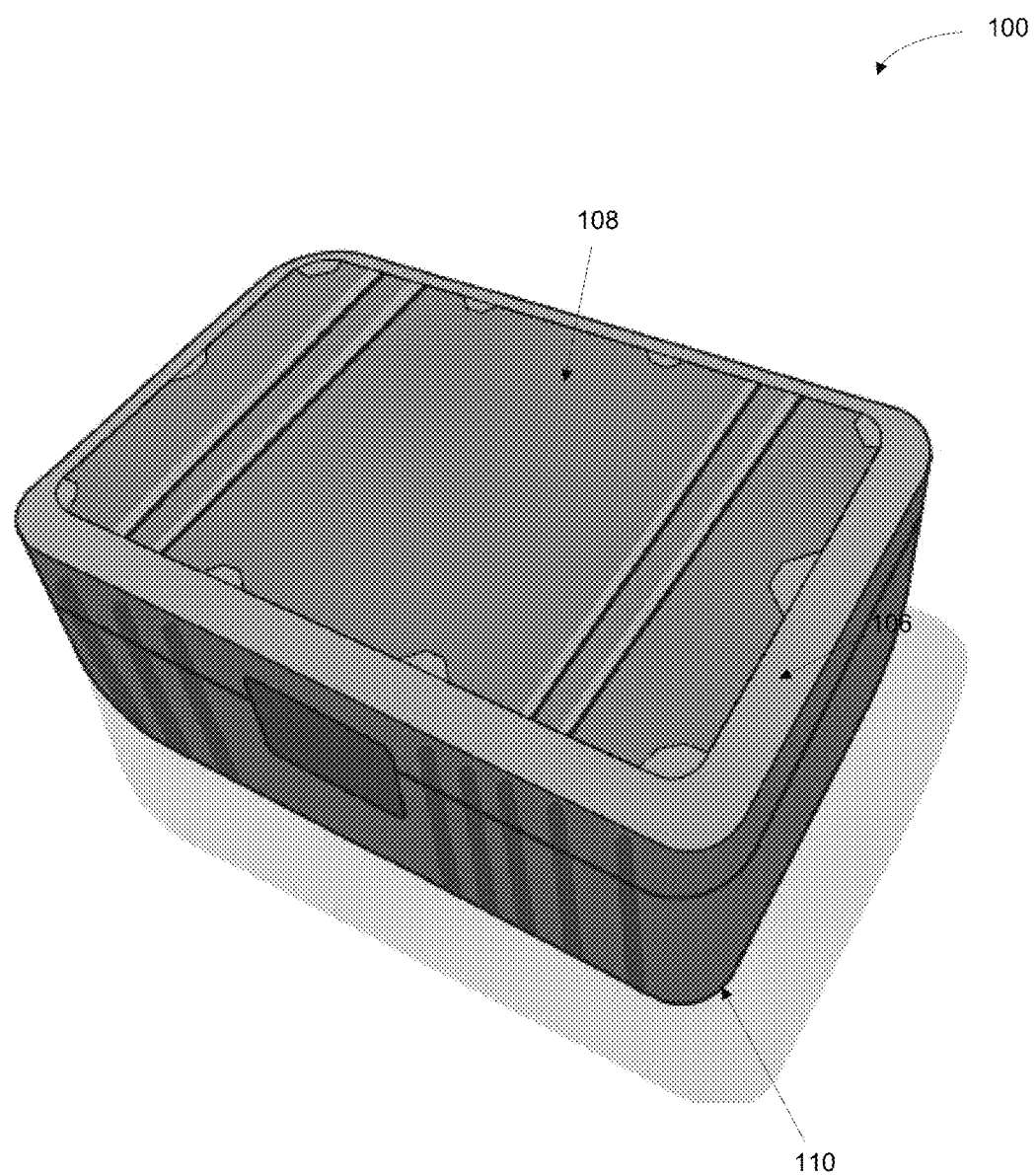
FIG. 2 shows the portable kit to illustrate the light bar that indicates a communicable status of the portable kit in accordance with an embodiment of the present disclosure.

FIG. 2 shows the portable kit to illustrate the light bar 106 that indicates a communicable status of the portable kit 100 in accordance with an embodiment of the present disclosure. A light bar 106 surrounds a portion of the kit. The light bar 106 may be formed by one or more LEDs having various colors or intensities with a light diffuser to give the appearance of a solidly lit bar 106. The light bar 106 may be illuminated with a variety of colors and intensities. The light bar 106 may also be illuminated with repeating or periodic patterns of color and/or intensities. For example, the light bar 106 may blink. In some embodiments of the present disclosure, one or more foldable legs may be pivotally connected to the kit 100 such that it may be stood on its side to form a table-like structure.

Figure 3:
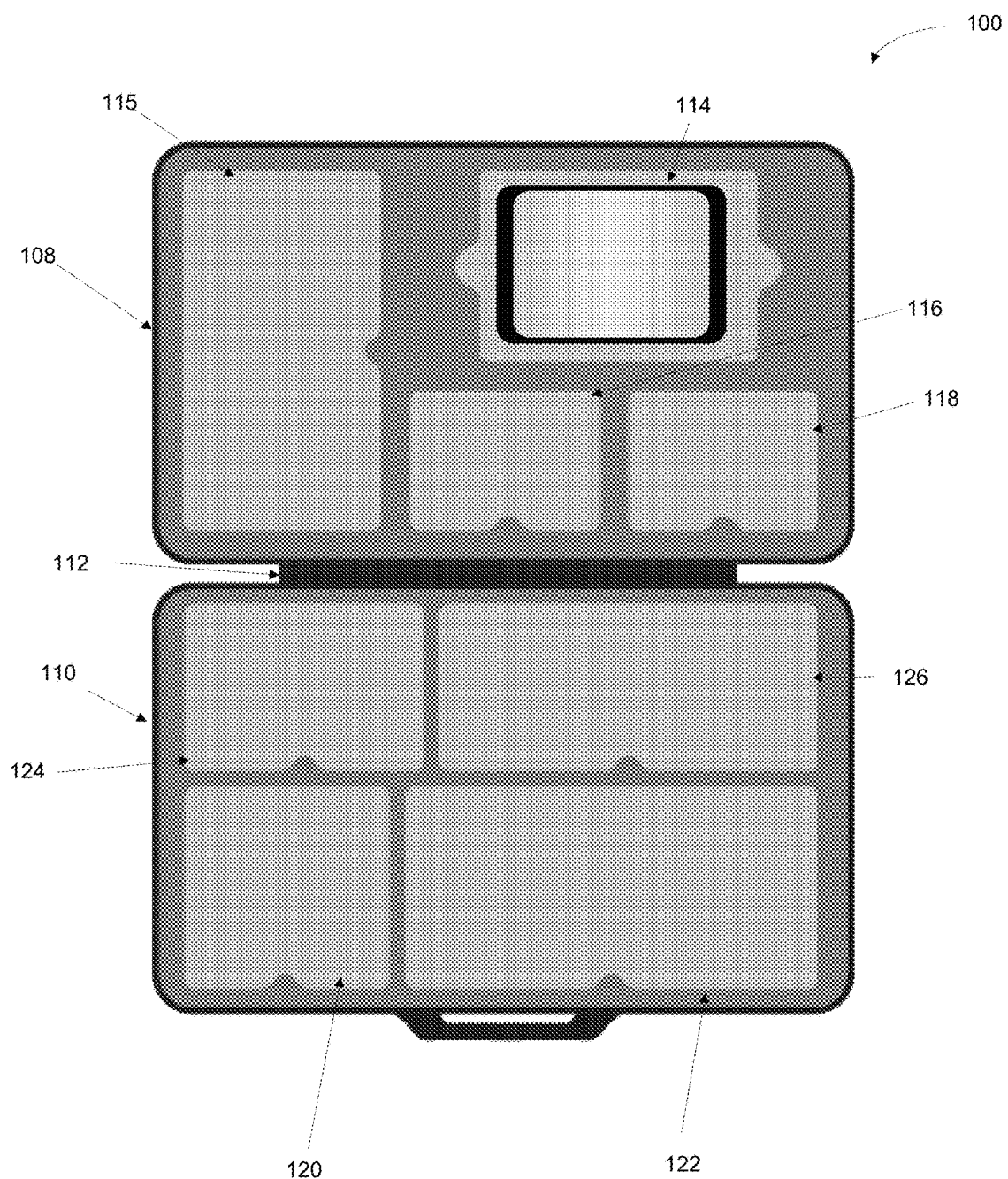
FIG. 3 shows an open portable kit to show the various compartments and a user interface in accordance with an embodiment of the present disclosure.

FIG. 3 shows an open portable kit 100 to show the various compartments and a user interface in accordance with an embodiment of the present disclosure. The kit 100 may be a "Universal" home kit. The "Universal" home kit may be a pre-packaged home care ecosystem that can be sent home with a patient as a result of a medical appointment and/or a caregiver-order prescription. For example, the kit 100 may be provided by a prescribing physician, institutional hospital, or retail healthcare clinic. The kit 100 may contain a set of integrated and easy to use medical equipment (i.e., medical apparatuses) appropriate for use in the home setting by a patient, family members and/or a licensed home caregiver.

The kit 100 may contain an integrated array of what is typically standalone equipment. The kit 100 may be sized to be about the size of a mid-sized travel suitcase as is typically used in air travel as a carry-on. The kit 100 has handles 102 and wheels 104 for ease of transport home by the patient (refer again to FIG. 1). As shown in FIG. 3, the kit 100 includes various compartments 115, 116, 118, 120, 122, 124, 126. The kit 100 also includes a user interface 114, e.g., a tablet. The kit 100 may include housing portions 108, 110 that are pivotable along a pivot (e.g., hinge) 112.

The kit includes a tablet 114 that may be a central control unit or may have a separate central control unit embedded within a housing portion 108, 110. The central control unit may incorporate a user interface, likely a touch screen graphical user interface, a cellular modem or other connectivity platform, Blue-tooth or other technology short-range interface radio(s). All of the medical apparatus found in the kit 100 may be pre-paired to the central control unit (e.g., tablet 114). Various medical apparatuses may be included within the kit 100, including, but not limited to, a weight scale, a pulse oximeter, a blood pressure meter, a thermometer, a blood glucose meter, a bioimpedance meter, and/or a spirometer. The tablet 114 may be pre-paired to all of the apparatuses over Bluetooth (e.g., Bluetooth LE).

The central control unit may provide a means for the kit to stream time-sequence data from the home directly into the electronic medical record. In some embodiments, the tablet 114 user interface provides "how-to" video support on demand, prompts users to perform care activities (such as changing dressings and taking medications), and serves as a channel for two-way communication between the patient and the licensed caregiver (telemedicine).

The medical apparatuses in the kit 100 may be an integrated platform. The kit 100 may limit the number of user interfaces the patient must learn by tight integration. By integrating the home care environment in the kit 100, the patient, in some embodiments, only needs to know how to use the tablet 114 and follow instructions provided on the tablet's 114 user interface based on the scenario at hand (e.g. taking a blood sugar reading when it is required).

The doors on the compartments various compartments 115, 116, 118, 120, 122, 124, 126 may open automatically. The doors may be transparent such that internal illumination can indicate to a user which compartment of the compartments various compartments 115, 116, 118, 120, 122, 124, 126 to open. In some embodiments, the doors of the compartments various compartments 115, 116, 118, 120, 122, 124, 126 are side illuminated.

In some embodiments, a power supply within the kit can power the medical apparatuses. The power supply may be connected to an AC outlet to provide inductive energy to the medical apparatus therein (or may power the devices directly through a wired connection). The power supply may include or be connected to a battery.

The tablet 114 or a central control unit may communicate data to a cloud server, which is accessible by a hospital, patient, and/or physician to retrieve data from a medical apparatus of any part of the kit 100.

In some embodiments, the kit includes an internal communications component, which may be an access point or hotspot for the tablet 114 and/or the medical apparatuses. The tablet 114 may be an access point or hotspot for the medical apparatuses and/or the communications components. The communication component and/or tablet 114 may include a secure link (e.g., encrypted and/or HIPPA compliant link) and/or an unsecured link.

In some embodiments, an environmental monitor component is disposed within the kit 100, which can monitor least one of temperature, humidity, location, vibration, shocks, and atmospheric pressure and communicate the measured parameter(s) to a cloud sever.

In some embodiments, an RFID reader is disposed within the kit 100. The RFID reader may communicate with the tablet 114 and/or the internal communications component. The RFID may be used to read RFID tags on the medical devices for inventory control purposes and/or to read RFID sensor values. An antenna may be in each compartment 115, 116, 118, 120, 122, 124, 126 such that the RFID reader can determine which of the compartments 115, 116, 118, 120, 122, 124, 126 the tag is located within The RFID reader may determine when supplies are low and communicate that data to the tablet 114 (or internal communications device) which then orders new supplies.

In some embodiments, access control of the kit 100 may be implemented, including fingerprint, password, voice, or other access control. In yet additional embodiments, an audible and/or visual alarm system may be included within the kit 100 which can alarm if an external signal from the cloud is received, an excessive number of failed access attempts have been initiated, and/or the tablet 114 determines that the alarm should be sounded (e.g., the kit 100 is taken outside of a specific geographic position, also referred to as a virtual fence determined by a geolocation module).

In some embodiments, the compartment will be illuminated to show the user which compartment should be used. The tablet 114 may automatically illuminate the next compartment when it determines that the medical apparatus has made its measurement to help the patient continue in the proper sequence of operation.

Figure 4:
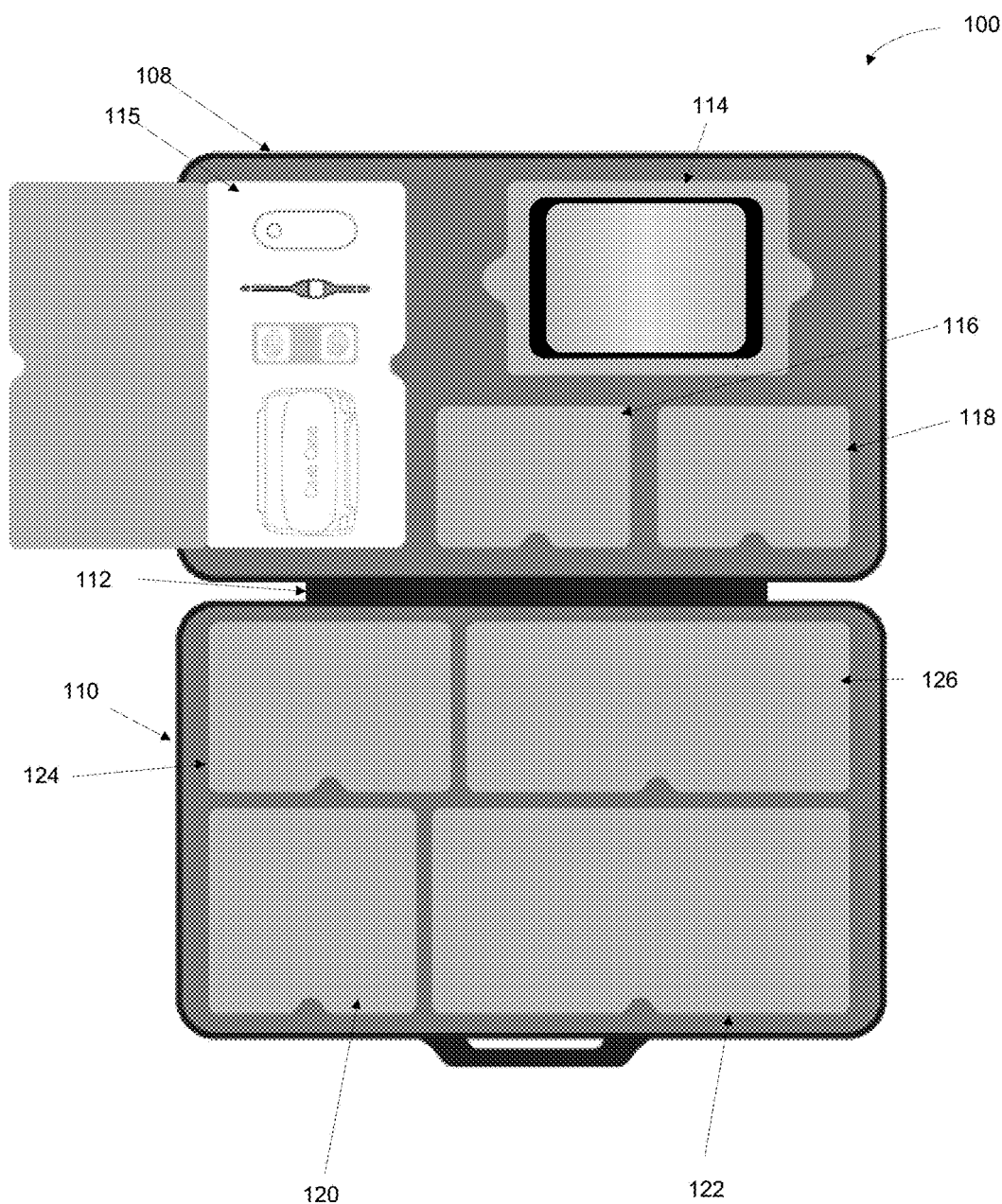
FIG. 4 shows an open portable kit with an open compartment having several physiological measuring devices in accordance with an embodiment of the present disclosure.

FIG. 4 shows an open portable kit 100 with an open compartment 115 having several physiological measuring devices in accordance with an embodiment of the present disclosure. Shown in the compartment 115 are a pulse oximeter, a thermometer, an EKG, and a blood pressure cuff.

Figure 5:
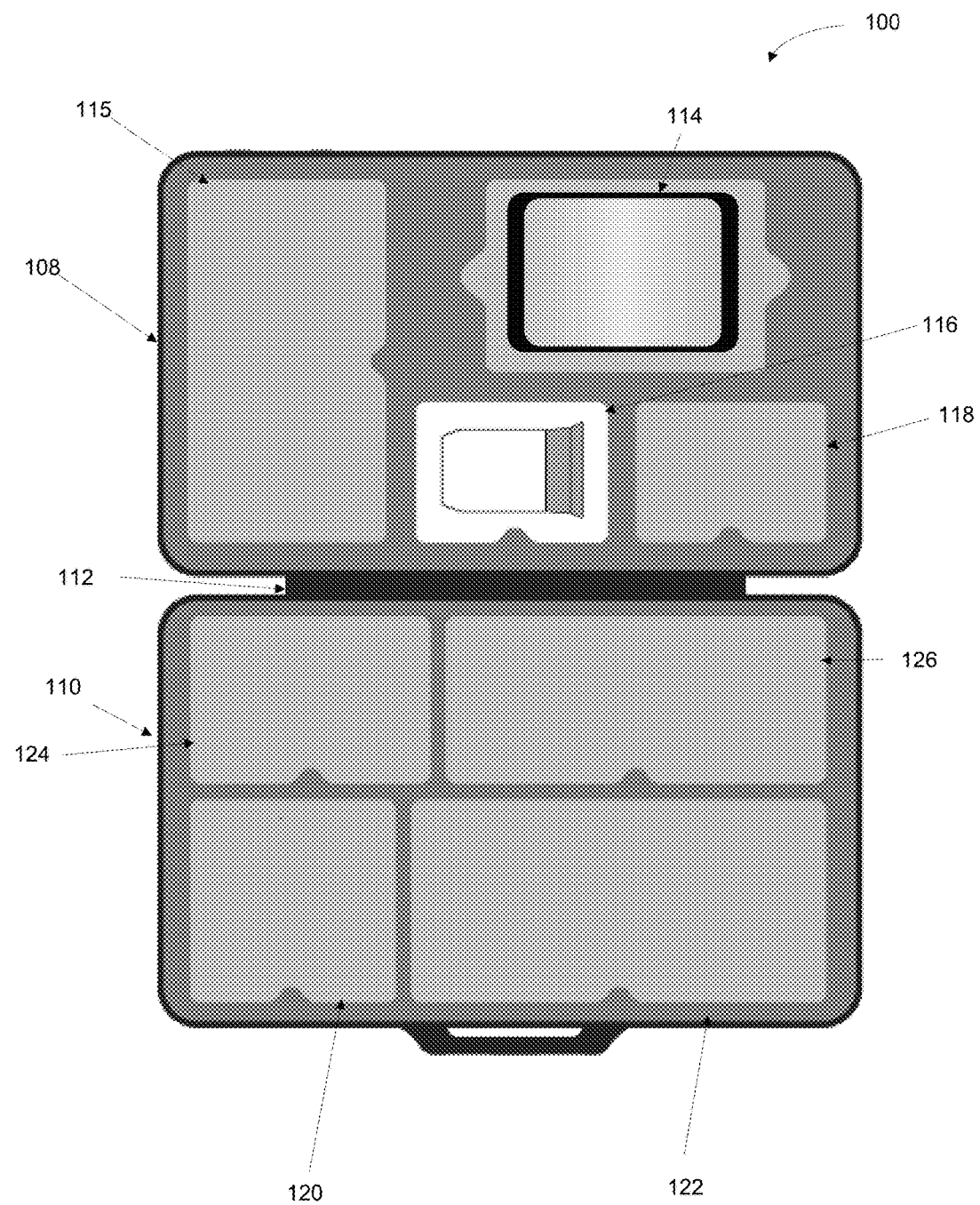
FIG. 5 shows an open portable kit with an open compartment having a pill dispenser in accordance with an embodiment of the present disclosure.

FIG. 5 shows an open portable kit 100 to a compartment 116 having a pill dispenser in accordance with an embodiment of the present disclosure. A physician may dispense a prescription that is received by the tablet 114 which in turn allows the pill dispenser to dispense a pill. The oral medicine dispensing device may be inserted into the kit 100 by a pharmacy where appropriately limited quantities of prescribed medications are included therewithin The dispensing rules of the oral medicine dispensing device 116 can be set (and changed) by a clinician through the central control unit remotely (e.g., the tablet 114).

Figure 6:
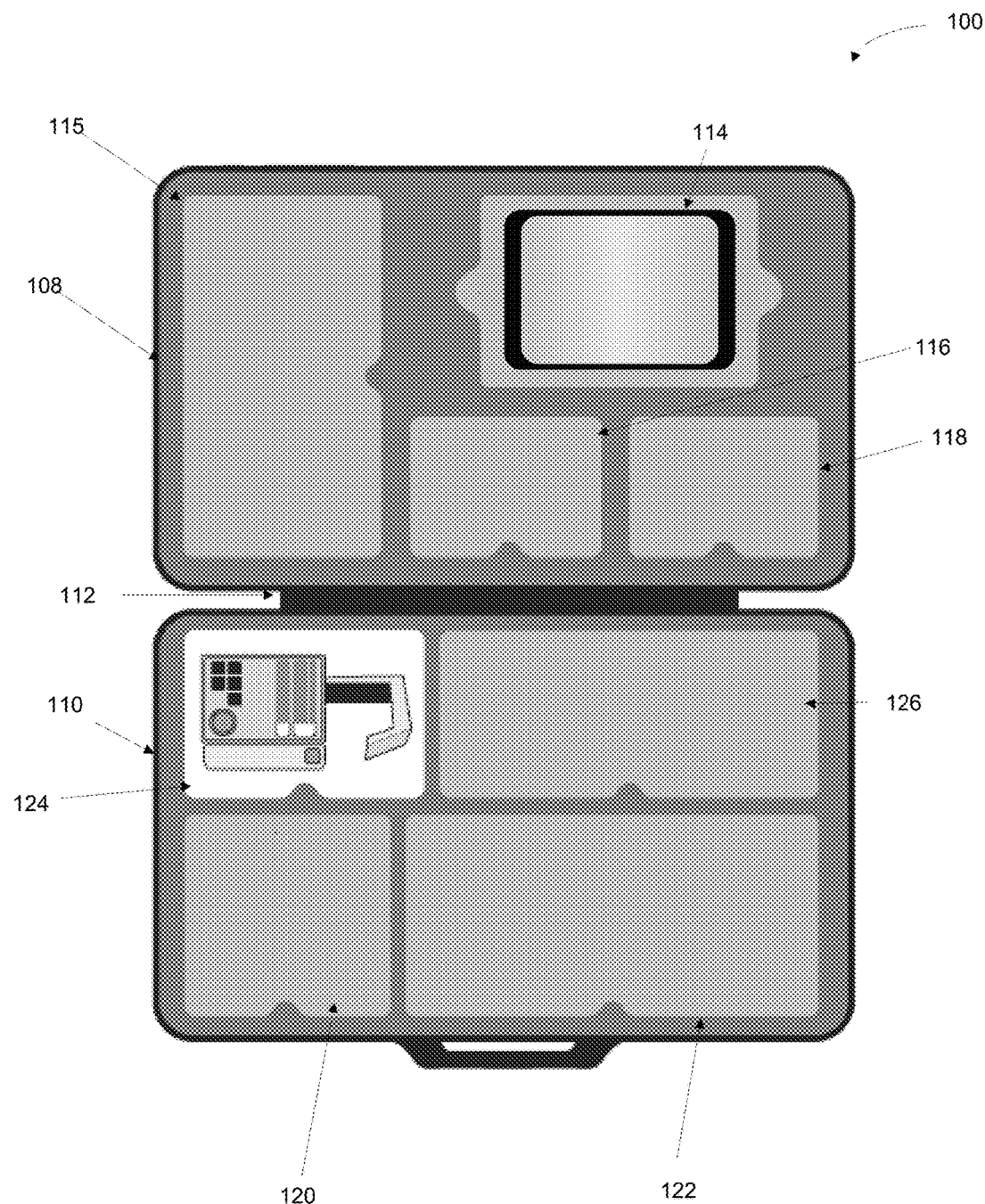
FIG. 6 shows an open portable kit with an open compartment having a gravity-based intravenous infusion pump in accordance with an embodiment of the present disclosure.

FIG. 6 shows an open portable kit 100 to a compartment having a mobile infusion pump (e.g., a gravity-based intravenous infusion pump) in the compartment 124. The mobile infusion device allows the patient or home caregiver to administer appropriate fluids (e.g. antibiotics) intravenously.

Figure 7:
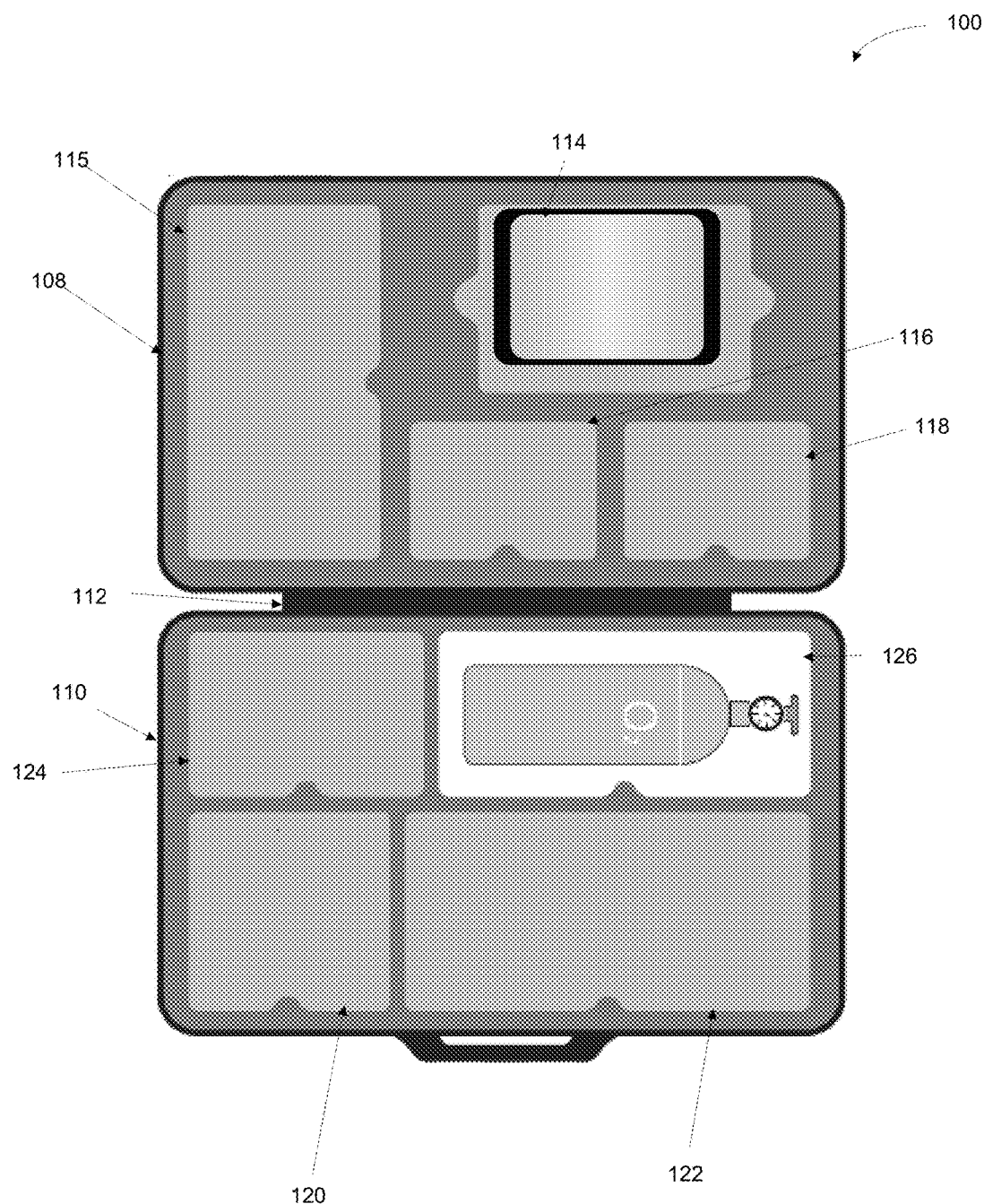
FIG. 7 shows an open portable kit with an open compartment having an oxygen tank in accordance with an embodiment of the present disclosure.
Figure 8:
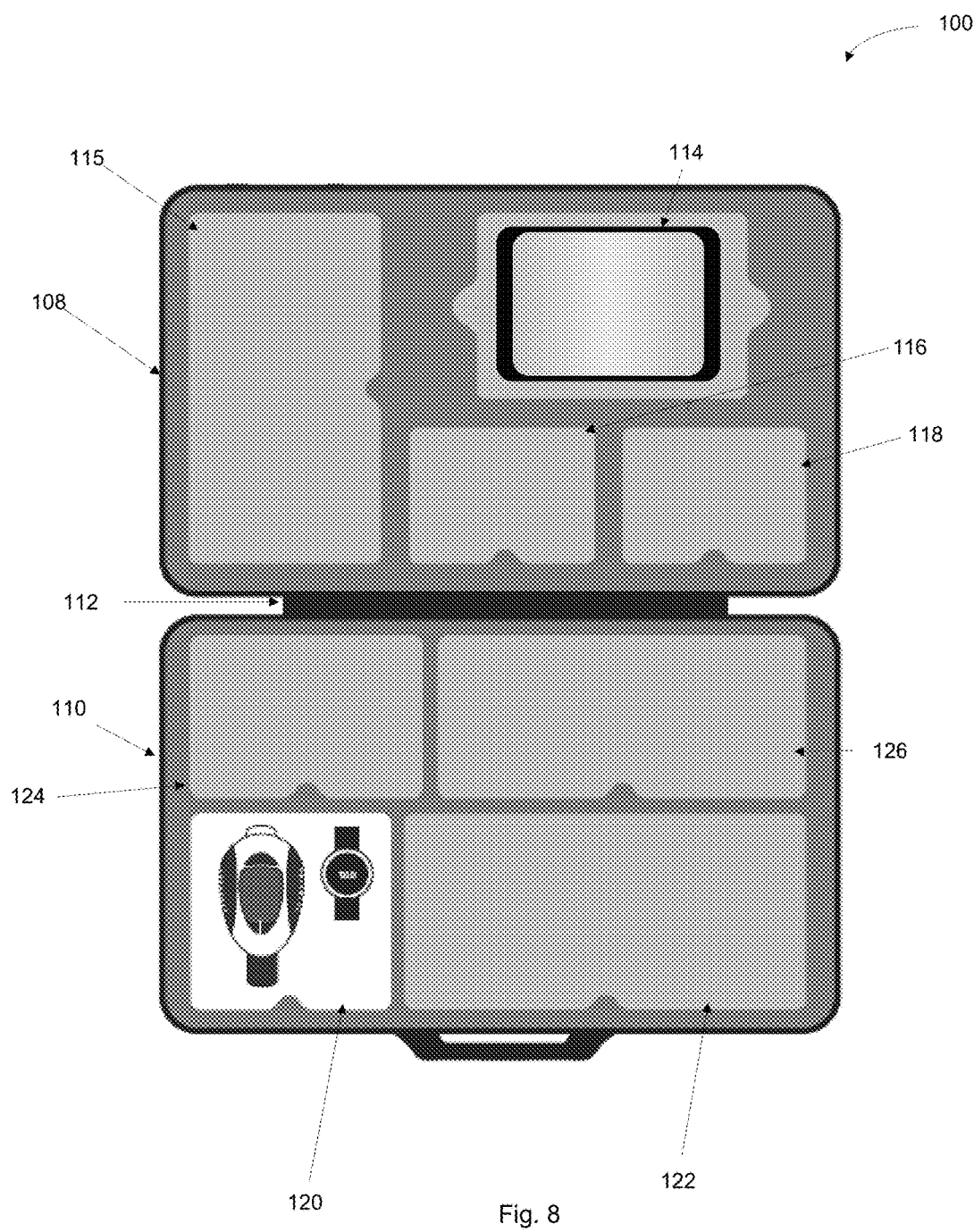
FIG. 8 shows an open portable kit with an open compartment having an activity monitor and a spirometer in accordance with an embodiment of the present disclosure.

FIG. 7 shows an open portable kit 100 to the compartment 126 having an oxygen tank. FIG. 8 shows an open portable kit 100 to a compartment 120 having an activity monitor and a spirometer in accordance with an embodiment of the present disclosure.

Various alternatives and modifications can be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. And, those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in the drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g., "a," "an," or "the," this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B. This expression signifies that, with respect to the present disclosure, the only relevant components of the device are A and B.

Furthermore, the terms "first," "second," "third," and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

What is claimed is:

1. A portable patient-care kit, comprising:
   two-housing portions pivotally coupled together to form a container space;
   a plurality of compartments disposed within at least one of the two-housing portions, each compartment configured to retain at least one medical apparatus;
   a central control unit comprising a touch-screen user interface device having a transceiver configured to communicate via a mobile data network; and
   a light bar disposed along an exterior of one of the two-housing portions configured to provide light;
   a plurality of lights, each of the plurality of lights being configured to supply light within a separate one of each of the plurality of compartments,
   wherein a compartment of the plurality of compartments includes a door, wherein the touch-screen user interface device is in operative communication with the door to instruct the door to automatically open, and
   wherein the central control unit is configured to illuminate the plurality of lights so as to illuminate the plurality of compartments and the at least one medical apparatus retained therein in a sequence of operation, the control unit configured to automatically illuminate a next compartment in the sequence of operation based on data from at least one of the at least one medical apparatus.

2. The kit according to claim 1, wherein a plurality of medical devices are stored at least one of the plurality of compartments, wherein the touch-screen user interface device is pre-paired with the plurality of medical devices, the plurality of medical devices including the at least one medical apparatus.

3. The kit according to claim 2, wherein the touch screen user interface device is pre-paired via a Bluetooth LE pairing schema.

4. The kit according to claim 1, wherein a housing portion of the two-housing portions includes a battery and a power supply configured to supply power to the at least one medical apparatus using the battery.

5. The kit according to claim 1, wherein the touch-screen user interface device is a tablet computer.

6. The kit according to claim 5, wherein the tablet computer is configured to teleconference with a physician having a computer device selected from the group of a PC, a second tablet computer, a smart phone, a terminal and a phablet.

7. The kit according to claim 5, wherein the at least one medical apparatus is at least one of a sphygmomanometers, a pulse oximeter, a photoplethysmogram, a thermometer, an electro cardiogram sensor, a blood glucose meter, a blood-based diagnostic meter, a urine sample container, and a blood collector container.

8. The kit according to claim 1, wherein any measurement of a person using one or more of the at least one medical apparatus is at least one of stored in a cloud server or communicated to a physician.

9. The kit according to claim 1, wherein a housing portion of the two-housing portions includes a communications component.

10. The kit according to claim 9, wherein the communications component is a hotspot.

11. The kit according to claim 10, wherein the touch-screen user interface device is a tablet computer, and the tablet computer uses the hotspot to communicate with a cloud server.

12. The kit according to claim 11, wherein the tablet computer communicates with the at least one medical apparatus and relays data therefrom to the cloud server.

13. The kit according to claim 12, wherein the tablet computer communicates the relayed data to the cloud server through the communications component.

14. The kit according to claim 13, wherein the at least one medical apparatus uses the tablet computer to communicate with the cloud server.

15. The kit according to claim 10, wherein the at least one medical apparatus communicates with the hotspot to transmit data to a cloud server.

16. The kit according to claim 1, wherein the touch-screen user interface device is a tablet computer and is configured to act as a hot spot.

17. The kit according to claim 1, further comprising an environmental monitor component.

18. The kit according to claim 17, wherein the environmental monitor component monitors at least one of a temperature, a humidity, a vibration, and a shock.

19. The kit according to claim 17, wherein the environmental monitor component communicates a monitored parameter to a tablet.

20. The kit according to claim 17, wherein the environmental monitor component communicates a monitored parameter to a cloud server.

21. The kit according to claim 20, wherein the environmental monitor component communicates the monitored parameter to the cloud server through an internal hot spot of the kit.

22. The kit according to claim 20, wherein the environmental monitor component communicates the monitored parameter to the cloud server through a tablet.

23. The kit according to claim 1, wherein at least one of the two-housing portions includes a communications component having a secure communications link and an unsecure communications link.

24. The kit according to claim 23, wherein the secure communications link communicates identifiable patient data.

25. The kit according to claim 23, wherein the unsecure communications link is an Internet link.

26. The kit according to claim 23, wherein the communications component is a hotspot.

27. The kit according to claim 26, wherein the hotspot is for at least one of the touch-screen user interface device and the at least one medical apparatus.

28. The kit according to claim 1, further comprising an RFID reader configured to record an inventory of the at least one medical apparatus.

29. The kit according to claim 1, further comprising an RFID reader configured to read a sensor value from an RFID tag.

30. The kit according to claim 1, further comprising an RFID reader configured to identify a user to allow a lock to unlock to gain access to a compartment of the plurality of compartments.

31. The kit according to claim 1, in which an RFID reader communicates with the touch-screen user interface device.

32. The kit according to claim 1, in which an RFID reader communicates with a communications component.

33. The kit according to claim 1, wherein a payment terminal is available including at least one of a debit card reader, a credit card reader, a health insurance card reader, or a money acceptor.

34. The kit according to claim 1, wherein there are four foldable legs to turn the opened kit into a table-like structure.

35. The kit according to claim 1, wherein an outer surface of the two-housing portions is at least one of magnetically shielding, electrostatically shielding, or electromagnetic shielding.

36. The kit according to claim 1, wherein the touch-screen user interface device is a tablet, wherein the tablet is configured to provide instructions to a patient how to use the at least one medical apparatus.

37. The kit according to claim 1, wherein at least one of the plurality of compartments is an environmentally controlled compartment configured to control at least one of temperature, humidity, pressure, or atmospheric composition.

38. The kit according to claim 1, wherein the touch-screen user interface device is a tablet, wherein the tablet is configured to teleconferencing with a physician.

39. The kit according to claim 1, further comprising an oxygen leak sensor.

40. The kit according to claim 1, further comprising an oxygen generator.

41. The kit according to claim 1, further comprising a communications component configured to connect to a wireless access point.

42. The kit according to claim 1, further comprising a communications component configured to interface with external medical apparatuses.

43. A portable patient-care kit, comprising:
two-housing portions pivotally coupled together to form a container space;
a plurality of compartments disposed within at least one of the two-housing portions, each compartment configured to retain at least one medical apparatus;
a central control unit comprising a touch-screen user interface device having a transceiver configured to communicate via a mobile data network;
a light bar disposed along an exterior of one of the two-housing portions configured to provide light;
a plurality of lights, each of the plurality of lights being configured to supply light within a separate one of each of the plurality of compartments; and
an RFID reader configured to record an inventory of the at least one medical apparatus, wherein each compartment includes a different antenna in which the RFID reader can determine which antenna of the plurality of antennas an RFID is in close proximity with to thereby determine which compartment the at least one medical apparatus is located,
wherein the central control unit is configured to illuminate the plurality of lights so as to illuminate the plurality of compartments and the at least one medical apparatus retained therein in a sequence of operation, the control unit configured to automatically illuminate a next compartment in the sequence of operation based on data from at least one of the at least one medical apparatus.

44. A portable patient-care kit, comprising:
two-housing portions pivotally coupled together to form a container space;
a plurality of compartments disposed within at least one of the two-housing portions, each compartment configured to retain at least one medical apparatus;
a central control unit comprising a touch-screen user interface device having a transceiver configured to communicate via a mobile data network;
a light bar disposed along an exterior of one of the two-housing portions configured to provide light; and
a plurality of lights, each of the plurality of lights being configured to supply light within a separate one of each of the plurality of compartments,
wherein a cover of a compartment of the plurality of compartments is configured to be side illuminated, and
wherein the central control unit is configured to illuminate the plurality of lights so as to illuminate the plurality of compartments and the at least one medical apparatus retained therein in a sequence of operation, the control unit configured to automatically illuminate a next compartment in the sequence of operation based on data from at least one of the at least one medical apparatus.

45. A portable patient-care kit, comprising:
two-housing portions pivotally coupled together to form a container space;
a plurality of compartments disposed within at least one of the two-housing portions, each compartment configured to retain at least one medical apparatus;
a central control unit comprising a touch-screen user interface device having a transceiver configured to communicate via a mobile data network;
a light bar disposed along an exterior of one of the two-housing portions configured to provide light; and
a plurality of lights, each of the plurality of lights being configured to supply light within a separate one of each of the plurality of compartments,
wherein a cover of a compartment of the plurality of compartments is automatically actuatable, and
wherein the central control unit is configured to illuminate the plurality of lights so as to illuminate the plurality of compartments and the at least one medical apparatus retained therein in a sequence of operation, the control unit configured to automatically illuminate a next compartment in the sequence of operation based on data from at least one of the at least one medical apparatus.

46. A portable patient-care kit, comprising:
two-housing portions pivotally coupled together to form a container space;
a plurality of compartments disposed within at least one of the two-housing portions, each compartment configured to retain at least one medical apparatus;

a central control unit comprising a touch-screen user interface device having a transceiver configured to communicate via a mobile data network;

a light bar disposed along an exterior of one of the two-housing portions configured to provide light; and a plurality of lights, each of the plurality of lights being configured to supply light within a separate one of each of the plurality of compartments, wherein the touch-screen user interface device is configured to receive a prescription from a physician via a communication link, the touch-screen user interface device is configured to authorize a pill dispenser within a compartment of the plurality of compartments to dispense the prescription, and wherein the central control unit is configured to illuminate the plurality of lights so as to illuminate the plurality of compartments and the at least one medical apparatus retained therein in a sequence of operation, the control unit configured to automatically illuminate a next compartment in the sequence of operation based on data from at least one of the at least one medical apparatus.

47. A portable patient-care kit, comprising:

two-housing portions pivotally coupled together to form a container space;

a plurality of compartments disposed within at least one of the two-housing portions, each compartment configured to retain at least one medical apparatus;

a central control unit comprising a touch-screen user interface device having a transceiver configured to communicate via a mobile data network;

a light bar disposed along an exterior of one of the two-housing portions configured to provide light;

a plurality of lights, each of the plurality of lights being configured to supply light within a separate one of each of the plurality of compartments; and an RFID reader configured to record an inventory of the at least one medical apparatus, wherein the touch-screen user interface device is configured to communicate a demand for new supplies to be delivered with a supply is below a predetermined threshold, wherein the central control unit is configured to illuminate the plurality of lights so as to illuminate the plurality of compartments and the at least one medical apparatus retained therein in a sequence of operation, the control unit configured to automatically illuminate a next compartment in the sequence of operation based on data from at least one of the at least one medical apparatus.

48. A portable patient-care kit, comprising:

two-housing portions pivotally coupled together to form a container space;

a plurality of compartments disposed within at least one of the two-housing portions, each compartment configured to retain at least one medical apparatus;

a central control unit comprising a touch-screen user interface device having a transceiver configured to communicate via a mobile data network;

a light bar disposed along an exterior of one of the two-housing portions configured to provide light; and a plurality of lights, each of the plurality of lights being configured to supply light within a separate one of each of the plurality of compartments, wherein the touch-screen user interface device is in operative communication with the light bar to at least one of control the color of the light bar and control the brightness of the light bar, and wherein the central control unit is configured to illuminate the plurality of lights so as to illuminate the plurality of compartments and the at least one medical apparatus retained therein in a sequence of operation, the control unit configured to automatically illuminate a next compartment in the sequence of operation based on data from at least one of the at least one medical apparatus.

49. A portable patient-care kit, comprising two-housing portions pivotally coupled together to form a container space;

a plurality of compartments disposed within at least one of the two-housing portions, each compartment configured to retain at least one medical apparatus;

a central control unit comprising a touch-screen user interface device having a transceiver configured to communicate via a mobile data network;

a light bar disposed along an exterior of one of the two-housing portions configured to provide light;

a plurality of lights, each of the plurality of lights being configured to supply light within a separate one of each of the plurality of compartments; and an audible alarm, wherein the touch-screen user interface device is configured to alarm the audible alarm if a signal is wirelessly communicated to the touch-screen user interface device indicating that the kit should alarm, wherein the central control unit is configured to illuminate the plurality of lights so as to illuminate the plurality of compartments and the at least one medical apparatus retained therein in a sequence of operation, the control unit configured to automatically illuminate a next compartment in the sequence of operation based on data from at least one of the at least one medical apparatus.

* * * * *